US010874364B2

(12) United States Patent
Pras et al.

(10) Patent No.: US 10,874,364 B2
(45) Date of Patent: Dec. 29, 2020

(54) APPARATUS AND METHOD FOR THREE-DIMENSIONAL INSPECTION OF AN OBJECT BY X-RAYS

(71) Applicant: Commissariat A L'Energie Atomique et Aux Energies Alternatives, Paris (FR)

(72) Inventors: Philippe Pras, Marcoussis (FR); Bertrand Rosse, Saint Maurice Montcouronne (FR); Pierre Raybaut, Antony (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 92 days.

(21) Appl. No.: 16/179,054

(22) Filed: Nov. 2, 2018

(65) Prior Publication Data

US 2019/0139244 A1 May 9, 2019

(30) Foreign Application Priority Data

Nov. 9, 2017 (FR) ...................................... 1760539

(51) Int. Cl.
*A61B 6/00* (2006.01)
*A61B 6/02* (2006.01)
(Continued)

(52) U.S. Cl.
CPC .............. *A61B 6/4429* (2013.01); *A61B 6/02* (2013.01); *A61B 6/035* (2013.01); *A61B 6/4405* (2013.01);
(Continued)

(58) Field of Classification Search
CPC .... A61B 6/00; A61B 6/02; A61B 6/03; A61B 6/035; A61B 6/08; A61B 6/12;
(Continued)

(56) References Cited

U.S. PATENT DOCUMENTS 3,910,124 A * 10/1975 Halsey .................. G01N 23/18
                                                          73/601
6,028,910 A   2/2000 Kirchner et al.
(Continued)

FOREIGN PATENT DOCUMENTS

DE          4235183 A1    3/1995
WO    WO 2009/153789 A1  12/2009

OTHER PUBLICATIONS

Search Report received in French application serial No. 170539 dated Jul. 27, 2018, 4 pages.

*Primary Examiner* — Anastasia Midkiff
(74) *Attorney, Agent, or Firm* — Brinks Gilson & Lione (57) ABSTRACT

An apparatus and method for three-dimensional inspection of an object by X-rays. The apparatus includes an X-ray generator and a digital imaging device spaced from each other by a distance which defines a magnification by 1 on the imaging device. The apparatus also includes a means for moving the X-ray generator and identically the imaging device by unitary movements in two orthogonal directions. Each unitary movement corresponds to an integer number fraction of the side of the imaging device, and obtains, by successive shots after each unitary movement, a matrix set of sub-images overlapping in the plane of extension of the imaging device. Each sub-image has a center with coordinates in a plane of magnification equal to N. An image processing means performs magnification of each sub-image and determines a stretch factor enabling the coincidence of the sub-images representing all or part of a predefined element of interest.

14 Claims, 6 Drawing Sheets

(51) Int. Cl.

| | | |
|---|---|---|
| *G01N 23/044* | (2018.01) | |
| *A61B 6/03* | (2006.01) | |
| *A61B 34/35* | (2016.01) | |
| *G06T 15/08* | (2011.01) | |
| *G01N 23/046* | (2018.01) | |
| *A61B 34/00* | (2016.01) | |
| *G06T 7/55* | (2017.01) | |

(52) U.S. Cl.
CPC .......... *A61B 6/4411* (2013.01); *A61B 6/4458* (2013.01); *A61B 34/35* (2016.02); *A61B 34/70* (2016.02); *G01N 23/044* (2018.02); *G01N 23/046* (2013.01); *G06T 7/55* (2017.01); *G06T 15/08* (2013.01); *A61B 6/025* (2013.01); *A61B 6/5241* (2013.01); *A61B 6/547* (2013.01); *G01N 2223/3303* (2013.01); *G01N 2223/427* (2013.01); *G06T 2207/10116* (2013.01); *G06T 2207/10124* (2013.01); *G06T 2207/30108* (2013.01)

(58) Field of Classification Search
CPC ......... A61B 6/40; A61B 6/4014; A61B 6/405; A61B 6/42; A61B 6/44; A61B 6/4405; A61B 6/4411; A61B 6/4429; A61B 6/4435; A61B 6/4441; A61B 6/4458; A61B 6/476; A61B 6/52; A61B 6/5211; A61B 6/5217; A61B 6/5235; A61B 6/5241; A61B 6/54; A61B 6/542; A61B 6/545; A61B 6/547; A61B 6/548; A61B 6/58; A61B 6/587; A61B 34/00; A61B 34/20; A61B 34/30; A61B 34/32; A61B 34/35; A61B 34/70; A61B 50/10; A61B 50/13; A61B 50/20; A61B 50/24; A61B 50/26; A61B 2562/16; A61B 2034/2046; A61B 2034/2055; A61B 2034/2059; A61B 2034/2072; A61B 2560/00; A61B 2560/02; A61B 2560/04; A61B 2560/0406; A61B 2560/0437; A61B 2560/0443; A61B 2560/0462; A61B 2560/06; G01N 23/00; G01N 23/02; G01N 23/04; G01N 23/044; G01N 23/046; G01N 23/06; G01N 23/083; G01N 23/10; G01N 2223/00; G01N 2223/03; G01N 2223/04; G01N 2223/076; G01N 2223/0766; G01N 2223/101; G01N 2223/1016; G01N 2223/30; G01N 2223/301; G01N 2223/308; G01N 2223/32; G01N 2223/321; G01N 2223/323; G01N 2223/33; G01N 2223/3303; G01N 2223/34; G01N 2223/40; G01N 2223/401; G01N 2223/402; G01N 2223/405; G01N 2223/41; G01N 2223/419; G01N 2223/427; G01N 2223/50; G01N 2223/639; G01N 2223/66; G01N 2291/028; G01N 2291/0289; G01N 2291/048; G01N 2291/052; G01N 2291/102; G01N 2291/26; G01N 2291/2695; G06T 7/00; G06T 7/0002; G06T 7/0004; G06T 7/001; G06T 7/50; G06T 7/521; G06T 7/55; G06T 7/5571; G06T 7/62; G06T 7/70; G06T 7/73; G06T 7/97; G06T 15/00; G06T 15/06; G06T 15/08; G06T 2207/00; G06T 2207/10; G06T 2207/10116; G06T 2207/10124; G06T 2207/30108; G06T 2207/30112; G06T 2210/41

See application file for complete search history.

(56) References Cited

U.S. PATENT DOCUMENTS

| | | | |
|---|---|---|---|
| 2003/0043962 A1 | 3/2003 | Lai | |
| 2004/0156476 A1* | 8/2004 | Halsmer | A61B 6/06 378/146 |
| 2010/0195868 A1* | 8/2010 | Lu | G02B 21/0084 382/103 |
| 2014/0016755 A1* | 1/2014 | Behiels | A61B 6/50 378/62 |
| 2015/0221080 A1 | 8/2015 | Yamamoto | |

* cited by examiner

| PV2 Analyses: | |
|---|---|
| Parameters | Results |
|  | Enlargement: 2.500 |
| D1: 307.0 cm |  |
|  | D2: 122.800 cm |
| D3: 200.0 cm |  |
|  | Depth: -77.200 cm |
| Stretch factor: 0.800 | |

Fig.9a

| PV2 Analyses: | |
|---|---|
| Parameters | Results |
|  | Enlargement: 1.429 |
| D1: 307.0 cm |  |
|  | D2: 214.900 cm |
| D3: 200.0 cm |  |
|  | Depth: 14.900 cm |
| Stretch factor: 1.4 | |

Fig.9b

| PV2 Analyses: | |
|---|---|
| Parameters | Results |
|  | Enlargement: 1.142 |
| D1: 307.0 cm |  |
|  | D2: 268.932 |
| D3: 200.0 cm |  |
|  | Depth: 68.932 |
| Stretch factor: 1.752 | |

APPARATUS AND METHOD FOR THREE-DIMENSIONAL INSPECTION OF AN OBJECT BY X-RAYS

RELATED APPLICATION

This application claims priority under 35 U.S.C. § 119 to French Patent Application No. 1760539, filed Nov. 9, 2017, the entire content of which is hereby incorporated by reference

TECHNICAL FIELD

The invention relates to the field of the three-dimensional inspection of objects by X-rays, in particular by digital radiography. It applies particularly to objects which cannot be moved and/or which have large dimensions relative to the dimensions of the imaging device that may be employed.

In particular, the invention relates to an apparatus for three-dimensional inspection of an object by X-rays, particularly a mobile apparatus, and to a method of using such an apparatus.

BACKGROUND

In the field of mobile radiography, the systems known from the state of the art may be distinguished and classified by taking into account two main criteria, which are the quality of the images they make it possible to obtain, and the ease of their implementation. The quality of the images refers in particular to the resolution of the system, its sensitivity, and the signal/noise ratio. The ease of implementation refers to characteristics such as the mass and the volume of the apparatus, the time required for its implementation both in terms of its installation and when measurements are made, and its robustness to the environment of use.

In addition to these criteria, it is very often desirable to be able to measure the depth, in the object, of sub-members of the X-rayed object. This is then referred to as three-dimensional inspection of the object.

Two broad families of known systems may be envisioned to perform mobile radiography, i.e. systems with photo-stimulable phosphor (PSP) plates, and digital imaging devices.

For the radiography of objects of large dimensions, systems with photostimulable phosphor (PSP) plates are well-suited. Indeed, the known systems employing this technology are sufficiently light to cover large surfaces by juxtaposition of several plates. Nevertheless, these systems provide a signal-to-noise ratio and sensitivity that are generally lower than those offered by the best digital imaging devices of the state of the art. Furthermore, as the reading of these plates is delayed, it is necessary to manually change the exposure configuration (generator and/or imaging device) to obtain three-dimensional information. This is detrimental to the rapidity of the operation.

Digital radiography imaging devices, also called digital X-ray imaging devices (with reference to the X-rays employed), enable images to be obtained instantaneously. The invention disclosed here implements this technology.

The images obtained by these systems are nevertheless of smaller dimensions compared with a juxtaposition of images that can be obtained in a PSP system. Furthermore, in the state of the art, the known systems are incompatible with the radiography of objects of large dimensions relative to the size of the imaging device, or having drawbacks in terms of ease of use or image quality.

As regards X-ray tomography, which by nature concerns the three-dimensional reconstruction of objects, several documents are known in the state of the art.

European patent number EP0037151 in particular is known which discloses a computer-assisted tomography device. European patent number EP 1356433 describes a method of reconstructing tomographic images. European patent number EP1838212 describes an apparatus and method for combined optical-coherence-tomographic and detection.

In general, in the approaches for three-dimensional reconstruction of objects envisioned in the prior art, a compromise is necessary between the mass and volume of the system on the one hand, and the required acquisition time on the other. As a matter of fact, either the number of detection and/or irradiation means is increased in the system, which enables measurements to be made in a limited time, but which is disadvantageous in terms of mass and volume of the system employed, or a limited number of detection and/or irradiation means is employed which are moved to perform multiple measurements around the object, but this is disadvantageous in terms of acquisition time and complexity of implementation of the system.

For the three-dimensional reconstruction of small objects, the systems employed may be mobile since they employ small X-rays generators and small digital imaging devices. This is for example the case in the orthodontic applications for which the diagnoses of patients must be fast. A single digital sensor may be employed in this case, with several X-ray sources. The following documents describe such applications:

U.S. Pat. No. 7,440,540 82, according to which two X-ray sources spaced apart by the width of the eyes irradiate a tooth of interest which is viewed as a three-dimensional image obtained in the visible spectrum; and U.S. Pat. No. 8,855,393 82, according to which three sources of X-rays are convergent on a tooth of interest which is modelled digitally by a post-processor.

In the applications for X-ray tomography of zones much wider than the human body, a single sensor is generally employed, of sufficient dimension.

U.S. Pat. No. 6,236,708 thus associates a single sensor with an X-ray generator which moves along a circle arc centered on the part of the body to diagnose. The multiplicity of images produced makes it possible to model the X-rayed part for it to be viewed. The required mechanical means for movement are imposing and mean the patient has to come towards the system, and not the contrary.

U.S. patent publication number 2013/0163719 discloses a similar apparatus, optimized as regards its mobility in order to be able to be moved along the corridors of a hospital. For this, two X-ray generators spaced by a fixed width are associated with a single imaging device. Viewing in three dimensions is direct and does not require a post-processor to provide it.

Nevertheless, such a system does not enable the radiography of objects of large dimensions, in that the size of the objects which it is able to x-ray is limited by the dimension of its imaging device. Furthermore, the system is not sufficiently robust for some applications, in particular those linked to security.

For the radiography of objects of very large dimensions, in particular vehicles, there is known for example by U.S.

Pat. No. 7,819,58082 a radiography gantry which is fixed, and under which the object to X-ray is moved.

For baggage control, for example in an airport, the U.S. Pat. No. 6,904,122 provides for the use of only one imaging device and only one X-ray generator the divergence of which is exploited. For this, the irradiation cone of the X-ray generator is collimated to create two X-ray brushes coming from the same source. The movement of the object generated by the baggage conveyor makes it possible to provide a multiplicity of shots and obtain the 3D information sought. On account of the collimators and the conveyor, this system is necessarily fixed.

For security applications in which it is not possible to move the object to check, the issue of obtaining the depth of the objects viewed with X-ray imaging in two dimensions also arises. For objects having a projected surface area less than the size of the digital imaging device, it is sufficient according to U.S. Pat. No. 8,976,926 to move the X-ray generator to obtain that information. In the system described in this document, the X-ray generator moves at the end of an arm movable over a circle arc in a plane parallel to the plane of the imaging device. The images obtained are superposed in a plane called "convergence plane" for the object of interest. The method thus proposed makes it possible to minimize the number of shots necessary to obtain the three-dimensional information sought, but it is not suitable for radiography of objects much bigger than the imaging device, unless the method concerned in this document is repeated numerous times.

A system for X-ray imaging of large dimension has been conceived to obtain the full radiography of imposing containers by means of digital imaging devices of smaller dimensions. Such a system is described by U.S. Pat. No. 7,800,061, wherein the generator and the imaging device are suspended by two cable systems in order to be always opposite each other around the container. The mechanics of the cables rests on the container to be checked which must be sufficiently strong to bear the imaging device and the X-ray generator. This method is unsuitable for the security applications that require rapidity, adaptability and absence of physical contact with the object to check.

It is apparent from this that, in the state of the art concerning the three-dimensional inspection of objects by X-rays, there is no known system enabling the inspection of objects of large dimensions by a mobile apparatus, while giving a high quality image and great ease of use.

SUMMARY

The invention disclosed seeks to resolve some or all of the aforementioned drawbacks.

Thus, the invention relates to an apparatus for three-dimensional inspection of an object by X-rays, comprising an X-ray generator and a rectangular or square digital imaging device facing said X-ray generator. The distance between the X-ray generator and the imaging device defines a magnification by 1, the X-ray generator being positioned on an axis orthogonal to a plane of extension of the imaging device, passing through the center of the imaging device. The X-ray generator is movable in a plane parallel to said plane of extension of the imaging device, and the imaging device is movable within its plane of extension.

The apparatus further comprises a means for controlling the position and the movement of said X-ray generator and of said imaging device configured so as to move the X-ray generator by unitary movements in a first direction or a second direction respectively parallel to the sides of the imaging device, and, at each unitary movement, to hold the relative position of the imaging device in relation to said X-ray generator, the control means being configured such that each unitary movement of the X-ray generator and of the imaging device, in the first or in the second direction, corresponds to an integer number fraction of the corresponding side of the imaging device (that is to say 1/N times the dimension of the side corresponding to the first direction and 1/N times the dimension of the side corresponding to the second direction, N being an natural number greater than 1, so as to obtain, by taking successive shots after each unitary movement, a matrix set of sub-images overlapping in the plane of extension of the imaging device.

In such an apparatus, each sub-image has a center attributed with coordinates in a plane of magnification equal to N, said coordinates being determined according to the position of the center of the imaging device on taking said sub-image, the apparatus further comprising image processing means configured to perform a homothetic magnification of each sub-image, leaving unchanged the coordinates of the center of each sub-image, said means being furthermore configured to determine a stretch factor enabling the coincidence of the sub-images representing all or some of a predefined element of interest of the image.

The coordinated movement of the X-ray generator and of the imaging device makes it possible to obtain images at the imaging device that overlap at least in part in a region of interest. The multiplicity of the two-dimensional information in this region makes it possible to determine its depth in the x-rayed object. The invention thus makes it possible to profit from the image quality of digital imaging devices, for example in terms of sensitivity and resolution, in particular in situations in which it is not possible or not desirable to move the inspected object. It is directed in particular to the inspection of objects of large dimensions. By configuring the unitary movements of the generator and of the imaging device, the invention enables adaptation to the situations in which only a small spacing away relative to the inspected object is available. The invention makes it possible to obtain three-dimensional information simply and rapidly.

The apparatus may comprise means for determining a depth and dimensions of the element of interest according to the determined stretch factor.

The apparatus may comprise a first mounting bearing the imaging device and a second mounting bearing the X-ray generator.

For example, the first mounting may comprise motor-driven wheels, configured to move the imaging device in the first direction, and a positioning means for positioning said imaging device in the second direction comprising a telescopic member or an arm along which the imaging device can translate, and the second mounting may comprise motor-driven wheels, configured to move the X-ray generator in the first direction, and a positioning means for positioning said X-ray generator in the second direction comprising a telescopic member or an arm along which the X-ray generator can translate.

In another embodiment, the first mounting comprises a first gantry and the second mounting comprises a second gantry, the first gantry comprising a first beam extending in the first direction, and a member bearing the imaging device extending in the second direction configured to position said imaging device in said second direction, said member bearing the imaging device being linked to the first beam so as to be able to be translated in the first direction, said member bearing the imaging device being a telescopic member or a second beam along which the imaging device is able to translate. The second gantry can then have an identical configuration to that of the first gantry and bear the X-ray generator instead of the imaging device of the first gantry.

In another embodiment, the first mounting comprises a first gantry and the second mounting comprises a second gantry, the first gantry comprising a first telescopic member extending in the first direction and a second telescopic member bearing the imaging device extending in the second direction configured to position said imaging device in said second direction, said second telescopic member being linked to the first telescopic member so as to be moved in the first direction by elongation or retraction of said first telescopic member, and the second gantry having a configuration identical to that of the first gantry and bearing the X-ray generator instead of the imaging device of the first gantry.

The first and the second mounting may each comprise an anti-tipping foot comprising a third beam, rigidly linked substantially orthogonally to the first beam.

The apparatus may comprise a laser aligning device enabling the relative alignment of the first and second mountings.

In another embodiment, the apparatus comprises a structure rigidly linking the X-ray generator and the imaging device, said structure between the X-ray generator and the imaging device, said structure being carried by a mounting comprising a system for moving said structure in the first direction and in the second direction. The system for moving the structure may comprise motor-driven wheels configured to move the structure in the first direction, and a mechanism comprising a telescopic member linked to the structure or an arm oriented in said second direction along which the structure is able to translate.

The invention also relates to a method of three-dimensional inspection of an object by X-rays comprising the steps of:
 providing an apparatus as described above;
 putting the apparatus in place in relation to the object, the X-ray generator and the imaging device being spaced from each other by a distance corresponding to a magnification by 1;
 obtaining a matrix set of sub-images;
 determining an element of interest of the object represented in said set of sub-images;
 determining, by homothetic magnification and partial superposition of the sub-images representing all or part of the element of interest, a stretch factor enabling the coincidence of the sub-images at the location of a point of interest; and
 determining a depth and dimensions of the element of interest according to the determined stretch factor.

This method may further comprise, between providing the apparatus and putting it in place,
 a step of determining the field of view necessary to X-ray the object,
 a step of determining the available spacing away in relation to a front face of the object for the putting in place of the X-ray generator; and
 a step of determining N according to the available spacing away and the dimensions of a region of interest containing the element of interest.

In such a method, N may be determined such that:
 if the region of interest is of greater dimension in the first direction than the fraction 1/N of the side of the imaging device corresponding to the first direction and is of greater dimension in the second direction than the fraction 1/N of the side of the imaging device corresponding to the second direction, N is the smallest integer, greater than 1, for which the spacing away is greater than 1/N times the distance between the X-ray generator and the imaging device, or
 if the region of interest is of smaller dimension in the first direction than the fraction 1/N of the side of the imaging device corresponding to the first direction or is of smaller dimension in the second direction than the fraction 1/N of the side of the imaging device corresponding to the second direction, N is the smallest integer for which the spacing away is greater than 2/N times the distance between the X-ray generator and the imaging device.

The method may also comprise a step of determining the number of shots n necessary with the imaging device to cover the field of view, without superposition of images, in the first direction and the number of shots m necessary with the imaging device to cover the field of view, without superposition of images, in the second direction, and for N=2 or N=3, the step of obtaining the matrix set of sub-images comprises obtaining N*n−3 to N*n+1 sub-images in the first direction and N*m−3 to N*m+1 sub-images in the second direction.

Other particularities and advantages of the invention will appear in the following description:

BRIEF DESCRIPTION OF THE DRAWINGS

In the accompanying drawings, given by way of non-limiting example.

DETAILED DESCRIPTION OF THE PREFERRED EMBODIMENTS

Figure 1:
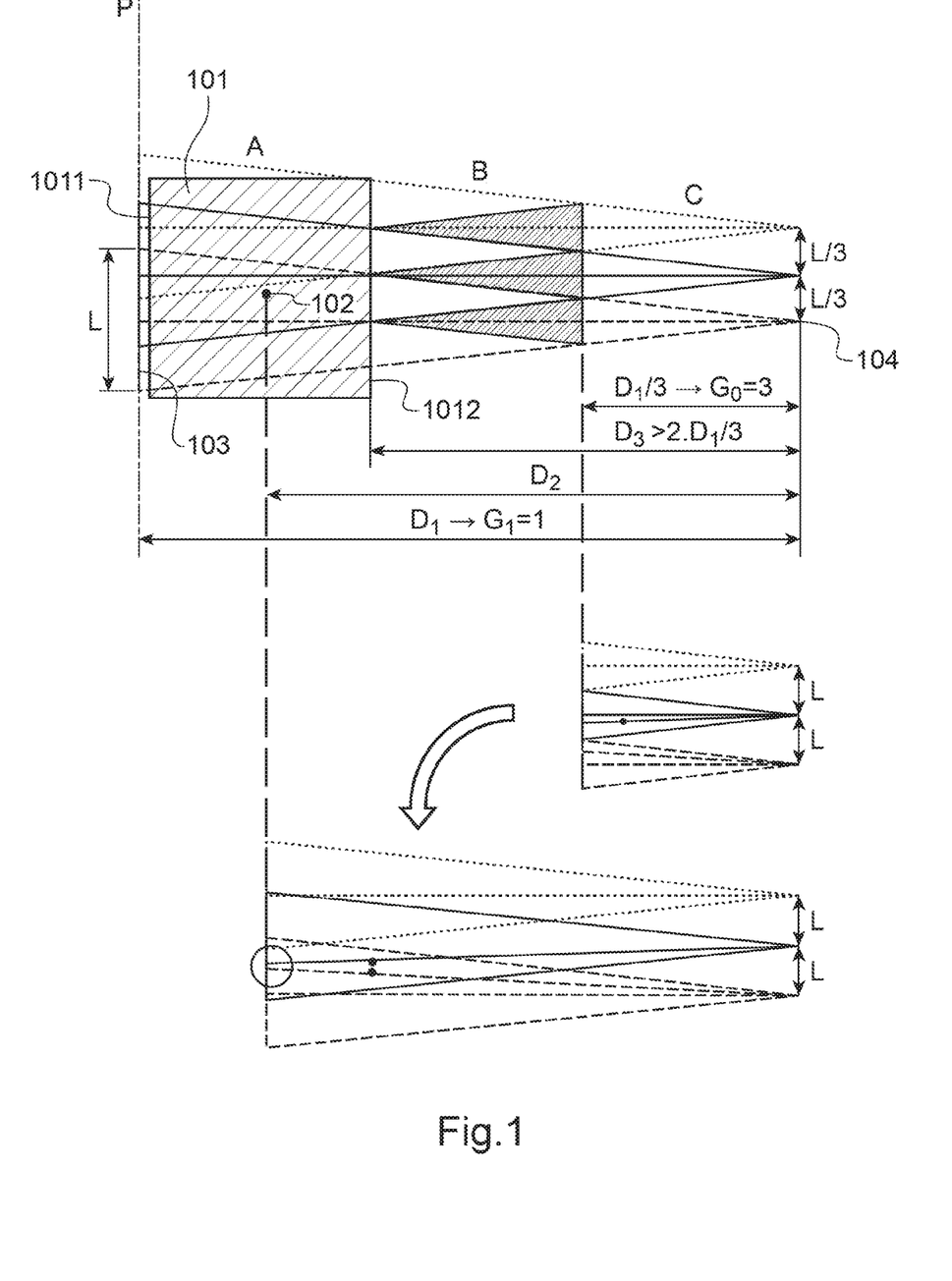
FIG. 1 illustrates in a diagram the principle implemented in the invention by a first example of application.

FIG. 1 illustrates in a diagram the principle implemented in the invention by a first example of application. The invention implements an apparatus of which detailed examples of embodiments are described in more detail with reference to FIGS. 5 to 8.

In FIG. 1, the object 101 to inspect, that is to say the object it is desired to check or diagnose is viewed from above. The object 101 is represented here in the form of a rectangle: this object may for example have a substantially right-angled parallelepiped shape.

Inside the object 101, an element of interest has to be x-rayed with accuracy. In the example represented here this is a member located at a point, constituting a point of interest 102. The depth of the point of interest 102 in the object must be determined in the context of the inspection.

According to the principle developed in the invention, a digital X-ray imaging device 103 is placed near the object, for example near a back face 1011. An X-ray generator 104, which may be called "source" is positioned opposite a front face 1012 of the object 101, in a suitable manner relative to the imaging device. In particular, the X-ray generator 104 is positioned on the axis passing through the center of the imaging device and orthogonal thereto (that is to say orthogonal to the plane of extension P of the imaging device 103), on the other side of the object 101 to the imaging device 103. The distance between the imaging device 103 and the X-ray generator 104 is referenced D1.

The distance D1 between the X-ray generator 104 and the imaging device 103 is such that there is no magnification in the plane of extension P of the imaging device 103, or, in other words, such that the magnification in that plane of extension P referenced G1 is equal to 1.

Based on the supposition that the imaging device 103 has a substantially rectangular surface, a pyramid is thus formed within the space (represented in FIG. 1) of which the apex is the X-ray generator 104 (which designates, for convenience of language, here and in the remainder of the present description, the emission point or "outlet" of said generator as an apparatus), and the base is the imaging device 103 (which designates, for convenience of language, here and in the remainder of the present description, the sensitive surface of the imaging device as an apparatus). The imaging device has a dimension L in a first direction (for example the width of the imaging device 103) and a dimension I in a second direction orthogonal to the first direction (for example the height of the imaging device 103).

The X-ray generator 104 is at a distance D3 from the most forward point of the object 101, that is to say its front face 1012 in the example represented here.

The distance, not known with accuracy before application of the invention, between the X-ray generator 104 and the point of interest 102 is referenced D2. More specifically, D2 corresponds to the shortest distance between the plane parallel to the plane of extension P of the imaging device 103 passing through the X-ray generator 104 and the point of interest 102.

The magnification with which the point of interest is viewed on the imaging device 103 is $G_2 = D_1 / D_2$.

Successive shots of the object are taken using the imaging device. Between each shot, the imaging device 103 is moved in its plane of extension, in a first direction (for example horizontally) or in a second direction (for example vertically). The X-ray generator 104 is moved correspondingly, simultaneously or not simultaneously, such that its relative position in relation to the imaging device 103 is unchanged at each shot.

Each movement of the imaging device 103, in the first or the second direction, corresponds to a predefined integer number fraction of the dimension of said imaging device 103 in that direction. For example, for a rectangular imaging device of width L, each unitary movement of the imaging device 103 in the direction parallel to the sides of the imaging device of width L corresponds to a distance 1/N times the width L (N being a natural number greater than 1). If the rectangular imaging device has a height I (dimension perpendicular to its width), each unitary movement of the imaging device in the direction parallel to the sides of the imaging device of height I corresponds to a distance of 1/N times the height I).

Therefore, the generator is moved correspondingly.

Unitary movements are thus made in a first direction and a second direction orthogonal to the first direction, each time a shot is made. Each shot is indexed according to its coordinates, for example the coordinates of its center in the plane of extension P of the imaging device 103. A matrix set of sub-images is thus obtained, of which an example is described below with reference to FIG. 9a.

In order to inspect an object 101 of large dimensions, a multiplicity of shots is necessary. According to the dimensions of the object, it is possible to determine the dimensions of the field of view necessary for its inspection, that is to say the dimensions in the plane of the imaging device which must be covered by the set of sub-images.

Figure 4:
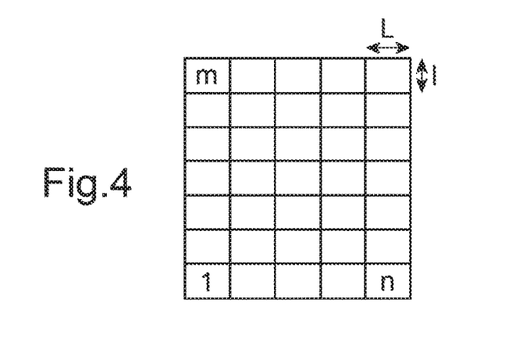
FIG. 4 diagrammatically illustrates one aspect of the invention.

For example, the required field of view may have a dimension n times L (L being the dimension of the imaging device 103 in the first direction) and a dimension m times I (I being the dimension of the imaging device 103 in the second direction). This example is illustrated in FIG. 4. If N was equal to 1 (which is excluded from the invention, and would correspond to a mere reconstitution of images on the basis of sub-images which do not overlap) n times m sub-images would be required (and thus the same number of shots) to X-ray the back of the object at least once. For any natural number N defining the fraction of the dimension of the imaging device in the first direction corresponding to a unitary movement in said first direction, N*n positions are typically required to analyze the content of the object in the first direction. Similarly, in the second direction, N*m positions are typically required to analyze the content of the object in the second direction. The number of shots necessary must nevertheless be adapted to the field of view to cover, according to the dimensions of the object and according to the region in which it is wished to take the shots, between a region referred to as "A" and a region referred to as "B" which are defined below. The number of shots is in particular configured in order not to lose information on the front face of the object. Thus, a subset of N*n by N*m sub-images is often necessary to cover the whole of the field of view, but the number of sub-images may in practice vary from N*n−3 to N*n+1 in the first direction and from N*m−3 to N*m+1 in the second direction, for N=2 or N=3.

Generalizing, for any integer 1≤a≤N, if the object has a height m−a/N<h/L≤m−(a−1)/N, there will be required N*m+2−a positions for the region referred to as "A" and N*m+1−a positions for the region referred to as "B". Certain mechanical constraints of a floor or a wall may lead to removing 1 position relative to these values.

In FIG. 1, N is equal to three. In the first direction, each movement of the imaging device and on a corollary basis of the generator in the first direction thus corresponds to one third of the width L of the imaging device 101, that is to say to L/3.

In FIG. 1, the imaging device 103 and the X-ray generator 104 have been represented respectively in three positions, each separated in the first direction by a distance L/3. The three positions are respectively represented with full line, with long dashes and with short dashes. The pyramids formed between the X-ray generator 104 and the imaging device 103 are viewed from above, and thus have a triangular shape with, as axis of symmetry, the straight line orthogonal to the plane of extension P of the imaging device passing through the X-ray generator 104.

In the direction parallel to the plane of extension P and orthogonal to the first direction (corresponding to the height in the imaging device in the example represented), the imaging device 103 and the X-ray generator 104 have a similar unitary movement, of one third the height I of the imaging device 104.

Three regions are thus defined:
- a first region A, for which each point of the object is x-rayed at least twice in two dimensions (at least four times in three dimensions with implementation of the orthogonal movement fractions);
- a second region B, in which each point is x-rayed at least once, and exactly once in the cross-hatched regions of FIG. 1; and
- a third region C, in which not all the points are x-rayed, and those points that are so are x-rayed only once.

In the example shown in FIG. 1, with N equal to three, the first region A is that for which the distance D to the X-ray generator is such that $D>2*D_1/3$.

The second region B is that for which the distance D to the X-ray generator is such that $D_1/3<D\leq 2*D_1/3$.

The second region C is that for which the distance D to the X-ray generator is such that $D_1/3<D\leq 2*D_1/3$.

Strictly speaking, D is a distance which is the shortest to the plane parallel to the plane of extension P, passing through the X-ray generator 104.

In the example represented here, the front face 1012 of the object 101 is positioned at the entry to the first region A, that is to say $D_3=2*D_1/3$.

The matrix set of sub-images obtained as explained earlier may then be the subject of image processing making it possible to determine the distance of the point of interest 102 or the depth of the point of interest 102 in the object 101.

The depth of the point of interest 102 in the object 101 corresponds to $D_2-D_3$.

The sub-images or partial images obtained are considered in the plane of magnification $G_0=N$. These processing operations may be automated or carried out by eye by an operator. As regards the processing by eye that is applied, of which the corresponding steps may be automated, reference may be made to FIGS. 9a to 9c which are described in more detail below.

The sub-images are thus viewed in the plane of magnification $G_0$. For this, the images are viewed by transparency or "tracing paper overlay", that is to say that the sub-images are viewed superposed in relation to each other, a sub-image of lower level remaining visible by transparency of the sub-image or sub-images of higher level. The position of the center of the sub-images is kept within the plane of magnification $G_0$. Thus, as illustrates the central part of FIG. 1, the sub-images are juxtaposed. The vertices of the pyramids, corresponding to the centers of the sub-images, are spaced apart by a distance L in the first direction and by a distance I in the second direction (only the first direction is visible in FIG. 1).

Each sub-image is stretched homothetically from its center of which the position remains unchanging. For a stretch factor F the projections of the point of interest onto several sub-images coincide. An image in the plane of the point of interest 102 is then obtained, as illustrated in the lower part of FIG. 1.

The stretch factor F can be identified interactively by eye by continuously varying the stretch factor by means of a dedicated software application until the two sub-images coincide at the point of interest. Automaton of this function is possible.

The magnification $G_2$ in a plane of the point of interest, is linked to the stretch factor F by the relation $F=N/G_2$.

The depth P of the point of interest is then determined by the formula $P=F*D_1/N-D_3$.

The principle described above may be applied for any point of interest observed over at least two sub-images. This principle is thus valid for any point of the object 101 which belongs to the first region A. It is only applicable for certain points of the second region B, i.e. the points present in a non-cross-hatched region of FIG. 1.

It follows that for the analysis of the elements of interest located at a point (for example the viewing of defects located at a point) the choice of N=3 is well-adapted, if the spacing away is sufficient for the point of interest to be in the first region A with certainty. In the opposite case the choice of a smaller integer number fraction (N>3) is possible as explained below in more detail, with reference to FIG. 3.

In the particular case in which the element of interest is of greater dimension, it is possible to use N=2, in the conditions and according to the provisions explained with reference to FIG. 2.

Figure 2:
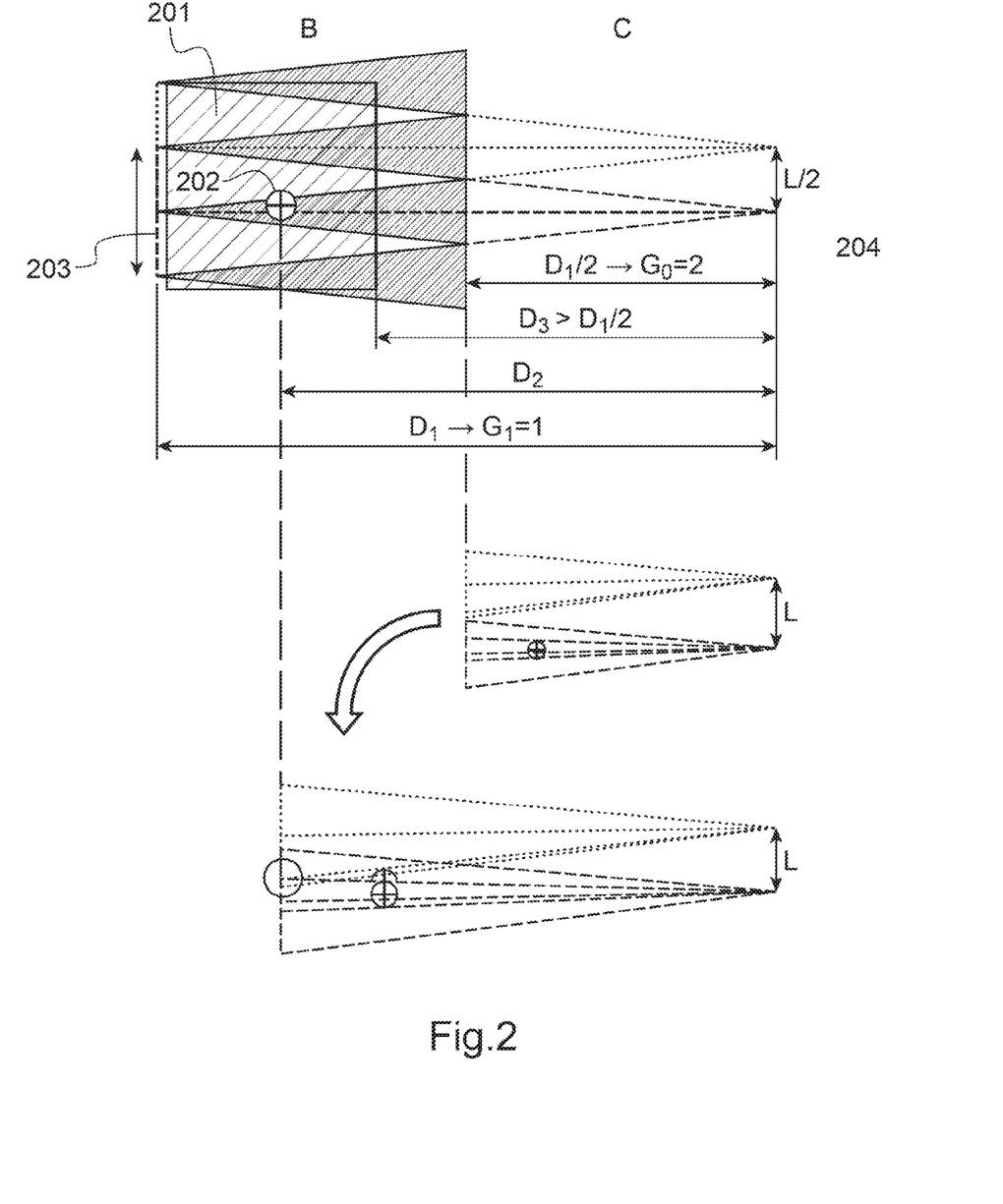
FIG. 2 illustrates in a diagram similar to that of FIG. 1 a second example of application.

FIG. 2 thus represents an optimization of the principle described with reference to FIG. 1 when the element of interest 202 in the object 201 (or the elements of interest 202) is sufficiently great. In particular, the dimension of the object 201 either in the first direction, or in the second direction, must be at least equal to the $N^{th}$ fraction of the dimension of the imaging device 203 in that direction. In other words, it is necessary for the object 201 to be greater than L/N in the first direction, or greater than I/N in the second direction.

If this condition is met, if the element of interest is located in the second region B, it is certain that every point of that element of interest will be x-rayed at least once, and that some points of the element of interest will be x-rayed at least twice, which makes it possible to obtain depth information for these points.

It will be noted that the second region B may be used in the aforesaid conditions, whether N be equal to 2 as illustrated in FIG. 2 or whether N be equal to 3 as illustrated in FIG. 1. Preference will be given to an embodiment wherein N=2 if the spacing away in relation to the object 101,201 is sufficient (as a matter of fact, the second region B begins for $D>D_1/2$ with N=2) while N=3 may be used if the spacing away is too small (the second region D begins for $D>D_1/3$ with N=3).

Figure 3:
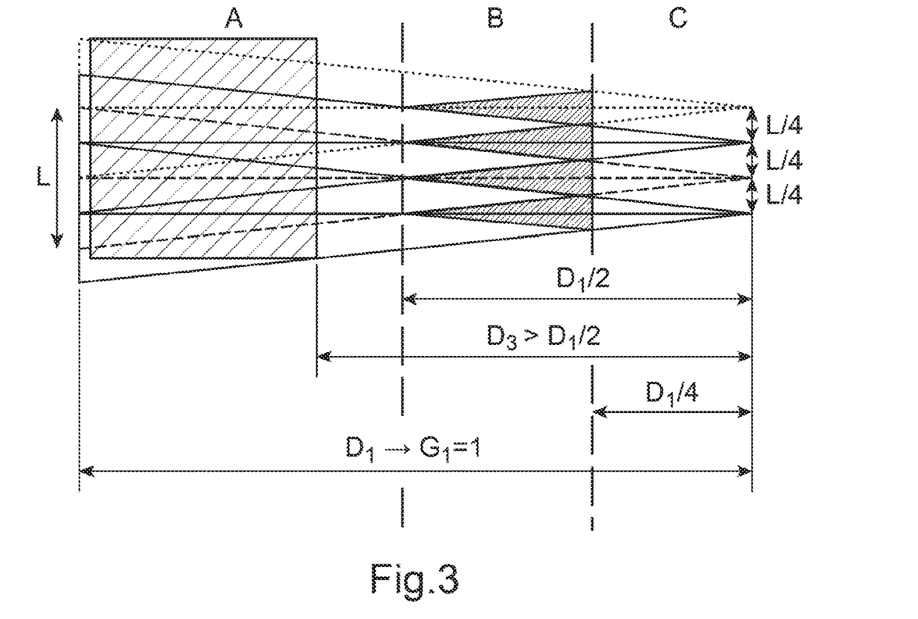
FIG. 3 illustrates in a diagram similar to that of FIGS. 1 and 2 a third example of application.

If a still smaller spacing away is available, a greater value of N, for example N=4 as illustrated in FIG. 3, may be employed. The second region B begins generally for $D>D_1/N$.

Similarly, the increase in the value of N may make it possible to ensure that an element of interest (typically located at a point) is situated in the first region A (which begins for $D>2*D_1/N$).

It is however desirable to minimize the value of N as much as possible. Indeed, the number of sub-images necessary to cover the whole of the desired field of view is typically N*n by N*m. Thus, the number of shots increases with the square of the value of N. This increases by the same amount the computation capacity necessary for the simultaneous processing of the sub-images. Furthermore, it is generally important to limit the exposure to the X-rays of the inspected object as much as possible.

The choice of N, as small as possible, is thus crucial to minimize the duration of measurement and the dose deposited on the object.

FIGS. 5 to 8 represent examples of embodiments of an apparatus in accordance with the invention, enabling the implementation of the principles described above with reference to FIGS. 1 to 4. In the context of a mobile apparatus, in all the examples presented below it is preferable to provide a battery supply, enabling convenient nomadic use of the apparatus.

The movable parts as well as the shooting may preferably be controlled at a distance, by wired or wireless means.

Figure 5:
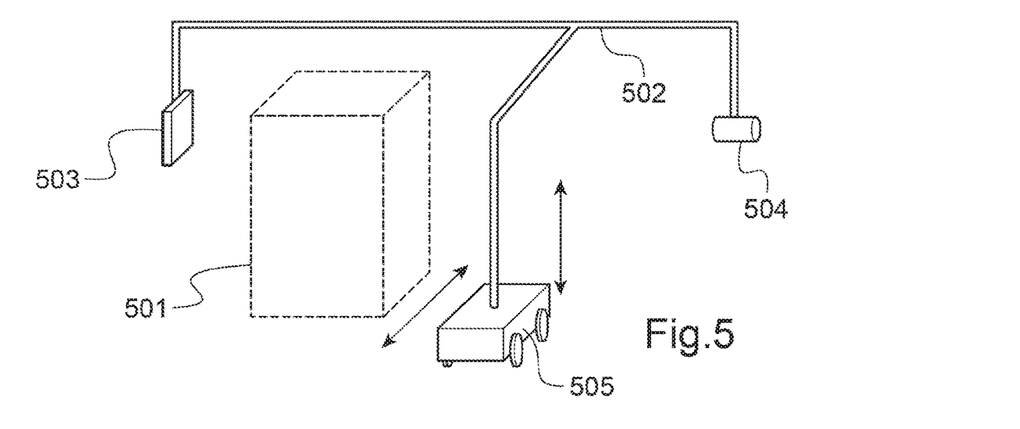
FIG. 5 illustrates, in a diagrammatic view in three dimensions, an apparatus in accordance with an embodiment of the invention.

FIG. 5 presents a first embodiment example. An object 501 to inspect is disposed on a substantially horizontal floor.

In this embodiment the X-ray generator 504 and the imaging device 503 are linked to each other rigidly by a structure 502 which bears them.

The structure 502 is of "C-shape" type, the X-ray generator 504 and the imaging devices 503 respectively being carried by a branch of the "C" formed by the structure.

The structure 502 is carried by a system for movement in the first direction and in the second direction. The system for movement comprises a robot 505. The robot 505 comprises motor-driven wheels configured to move the structure in the first direction, and a mechanism comprising means for vertically moving the structure 502. For example, the robot 505 may comprise a telescopic member linked to the structure 502, or an arm oriented in the second direction (here the vertical) along which the structure may be translated. If a telescopic member is employed, its elongation or its retraction enable the movement of the member it bears along its extension axis. If an arm is employed, it may bear a toothed slide or an equivalent device along which the carried member can translate In general terms, the telescopic members employed in this embodiment as well as in the other embodiments of the invention, may be linear actuators (each telescopic member being formed by an actuator or comprising several actuators longitudinally associated), or telescopic arms comprising several segments movable in relative translation, and able to be disposed one inside the other or one along the other. Several telescopic members may be joined end-to-end to provide greater travel.

The horizontal and vertical movements may thus be indexed accurately by a robot 505 for example.

The apparatus is configured to ensure that the movements are indeed made in the plane parallel to the imaging device and that the X-ray generator does indeed point the center of the imaging device on an axis orthogonal to its sensitive surface.

Given the weight and volume of the X-ray imaging devices and generators known in the state of the art, the configuration presented in FIG. 5 requires the robot to be weighted to a significant extent due to the cantilevered mounting of the structure 502. Furthermore, a high rigidity of the apparatus is required to enable the taking of clear images and sufficient positioning accuracy to enable good superposition of the sub-images.

Figure 6:
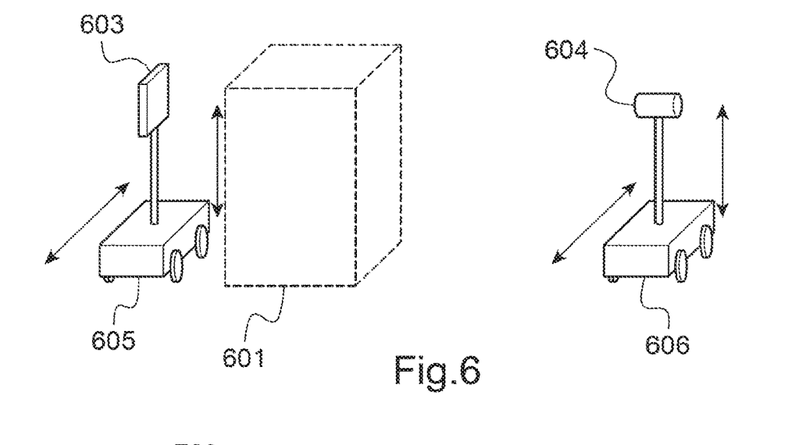
FIG. 6 illustrates, in a diagrammatic view in three dimensions, an apparatus in accordance with an embodiment of the invention.

FIG. 6 represents another embodiment of an apparatus in accordance with the invention. In this embodiment, a first robot 605 forms a first mounting for the imaging device 603, and a second robot 606 forms a second mounting for the X-ray generator 604. The first robot 605 and the second robot 606 are positioned on opposite sides of the object 601 to inspect.

The robots 602 and 603 are able to move in similar manner, which respectively moves the digital imaging device 603 and the X-ray generator 604.

In this configuration, the movements are not necessarily synchronous, but the appropriate relative positioning between the imaging device 603 and the X-ray generator 604 must be provided at each shot.

By their motor-driven wheels, the robots provide the horizontal movement of the imaging device 603 and of the X-ray generator 604.

For the vertical movement, each robot is equipped with a telescopic member or an arm oriented in said second direction along which the imaging device and the X-ray generator can translate.

Figure 7:
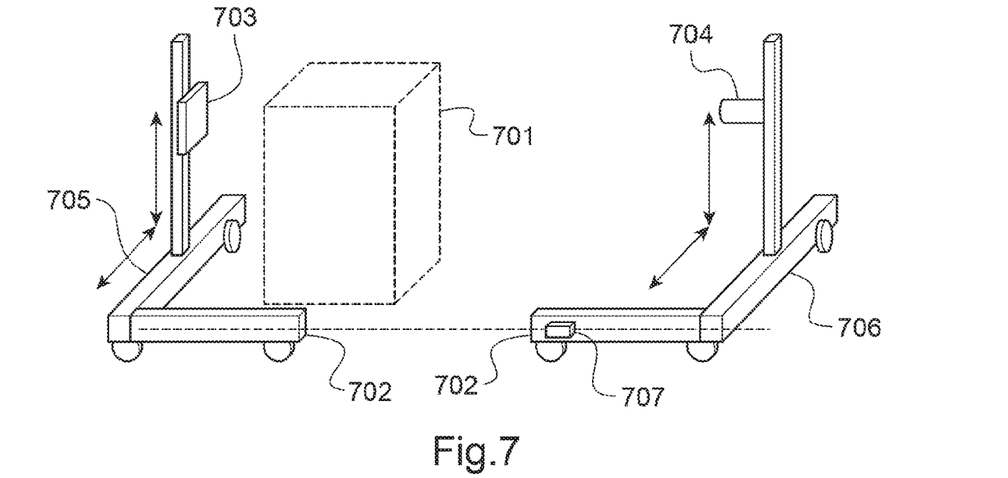
FIG. 7 illustrates, in a diagrammatic view in three dimensions, an apparatus in accordance with an embodiment of the invention.

FIG. 7 represents another embodiment of an apparatus in accordance with the invention. In this embodiment, a first mounting 705 bears the imaging device 703, and a second mounting 706 bears the X-ray generator 704.

The mountings are of gantry type, and enable a movement in the first direction (for example horizontal, in the plane of extension of the imaging device) and in the second direction (for example vertical) of the member they bear.

Each mounting comprises for this a first beam extending in the first direction, and a second beam bearing either the imaging device 703 or the X-ray generator 704 extending in the second direction. The second beam is linked to the first beam so as to be able to be translated in the first direction. The imaging device 703 or the X-ray generator 704 may be translated along the second beam, in the second direction.

The first mounting 705 and the second mounting 706 are paired, and the movements of the imaging device 703 and of the X-ray generator 704 are synchronized.

The second vertical beams may be replaced by a vertical telescopic member.

The gantries comprise an anti-tipping foot 702, substantially orthogonal to the first direction and to the second direction. The first gantry and the second gantry may be aligned with each other, for example by relative alignment of their anti-tipping feet. This alignment may be carried out by eye, or using a laser device 707.

For example lasers may be placed at the ends of the anti-tipping feet 702 and be mechanically aligned with them. The impact of the laser on a target identified on the foot of the facing mounting enables the relative alignment of the first and second mountings. A single laser 707 may be employed, a mirror positioned on the opposite mounting enabling alignment by self-collimation.

In the example embodiment of FIG. 7, the mountings are movable on multidirectional wheels in order to bring the system near the object and facilitate the alignment operations. This design is low-cost relative to multi-function robots. Furthermore, the space required behind the object 701 (that is to say adjacent the imaging device) to interpose the first mounting 705 between the object and an obstacle such as a wall is less great than in the configuration represented in FIG. 6. Furthermore, the configuration presented in FIG. 7 enables perfectly rectilinear guiding along the first and second beams.

Figure 8:
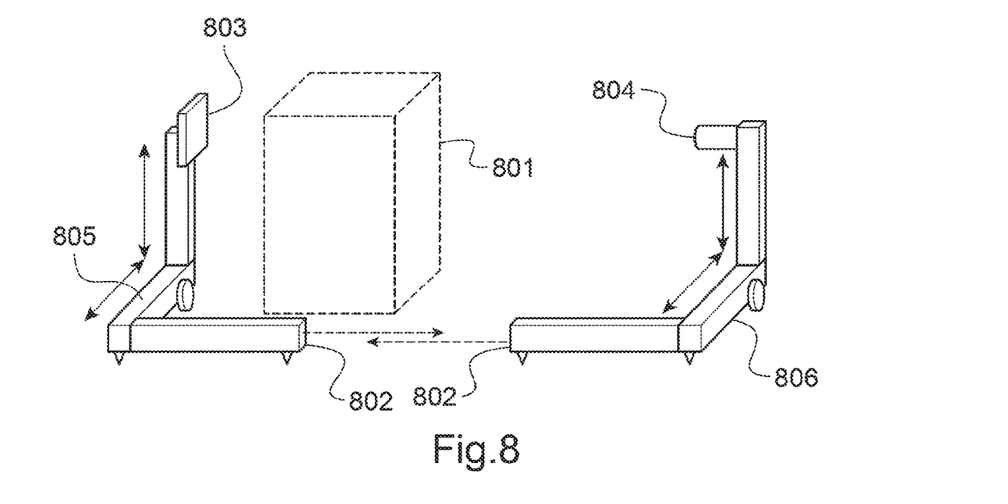
FIG. 8 illustrates, in a diagrammatic view in three dimensions, an apparatus in accordance with an embodiment of the invention.

FIG. 8 represents another embodiment of an apparatus in accordance with the invention. This embodiment is rather similar in its general configuration to that represented in FIG. 7. It comprises a first mounting 805 which bears the imaging device 803, and a second mounting 806 which bears the X-ray generator 804.

The mountings are of gantry type, and enable a movement in the first direction (for example horizontal) and in the second direction (for example vertical) of the member they bear.

In this embodiment, the anti-tipping feet 802 are placed on height-adjustable jointed mountings instead of the wheels of the embodiment of FIG. 7.

Each mounting comprises a first telescopic member extending in the first direction on which is fastened a second telescopic member extending in the second direction. In the example represented here, the second telescopic member is fastened at the end of the first telescopic member. A mounting wheel enabling the horizontal linear guiding on elongation or retraction of the first telescopic member. A rail, not shown, can be put in place to guide the wheel.

The apparatus of FIG. 8 has greatly reduced bulk for its transport, while enabling lengthy travel of the imaging device and of the X-ray generator during its use.

The alignment of the first and second mountings may be carried out as described with reference to FIG. 7.

The apparatuses according to the different embodiments described, in particular those of FIGS. 7 and 8, may be dimensioned so as to be able to be transported on a standard pallet of 80 cm by 120 cm, or in the trunk of an automotive vehicle of average size.

The inspection of an object by an apparatus as described above requires an image processing device enabling operations to be performed in real time on the set of sub-images obtained.

The analysis software employed for the images has functionalities such as: the reading and recording of an image, the adjustment of contrast, the possibility of zooming to view the finest details, a function of superposing shapes (line segments, circles, ellipses, rectangles, etc.) of dimensions that are known in terms of pixel numbers in order to measure image regions.

A specific image processing function makes it possible to interactively manipulate (translate, stretch, rotate from the center, etc.) typically N*n by N*m partial images simultaneously. Each image may have a size of several Mega-bytes. Such a software application may be implemented by a computer, for example a portable computer. The software and the computer system employed must preferably be capable of modifying multiple voluminous images simultaneously with a computing time of the order of a few milliseconds in order for the graphical modifications to be perceived without delay by the user.

A specific graphical interface makes it possible to open the set of sub-images acquired and to juxtapose them in the plane of magnification $G_0=N$ on a typical matrix of N*n columns and N*m rows (the number of rows and columns being configured to the number of actual shots) which is called "sub-image mosaic".

Figure 9A:
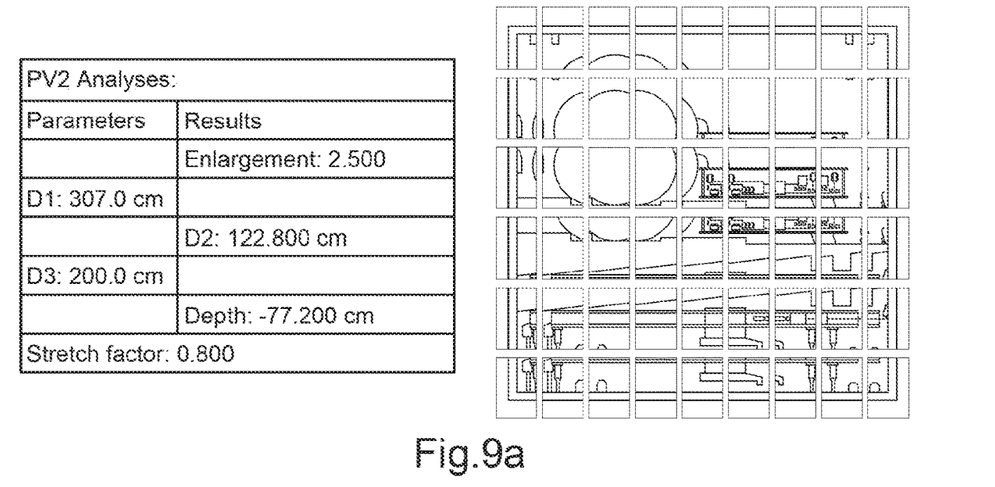
FIGS. 9a to 9c illustrate the improved processing carried out in an embodiment of the invention.

In FIG. 9a there is shown a mosaic of sub-images arising from the radiography of a cubic object of one cubic meter containing a ball of 36 cm diameter (which constitutes the element of interest) and electronic devices. In this example N=2.

In FIG. 9a the sub-images are represented for a stretch factor F equal to 0.8. The sub-images would be juxtaposed against each other for a stretch factor F equal to 1, and a magnification by 2.

In order to be capable of transforming dimensions in pixels into dimensions in cm for example, the software has an interface with the operator to provide the values of D1 and D3 physically measured for the configuration of the study. In the example presented here, the graphical interface (on the left) makes it possible to enter the values of D1 (here 307 cm) and of D3 (here 200 cm) which correspond to the configuration of the apparatus at the time of the acquisition of the set of sub-images.

The software may be configured so as to give the user good ergonomics and great ease of use. For example, the manipulation of a cursor can make it possible to continuously vary the size of each sub-image for a same stretch factor F. When the superposition of the sub-images is correct at the location of an element of interest, the software performs the magnification G associated with the current stretch factor F and the depth P of that element of interest in the inspected object.

Figure 9B:
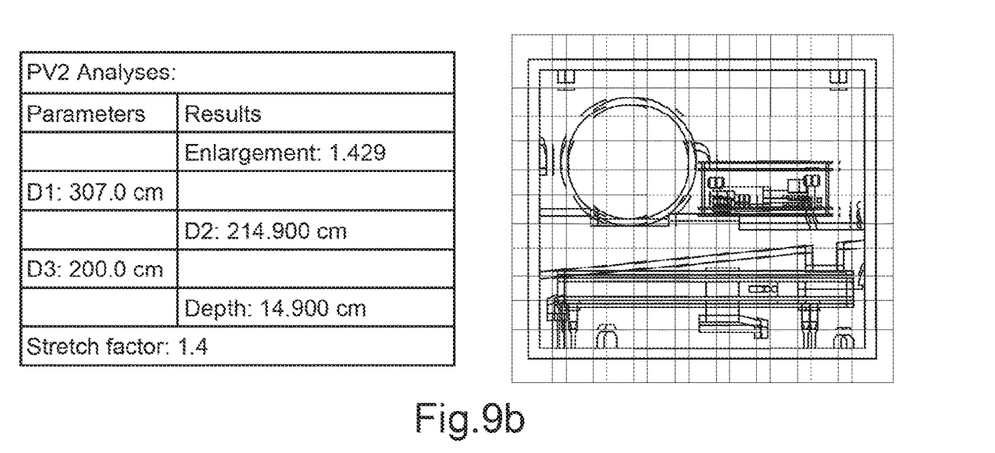

In FIG. 9b, the stretch factor of the 35 images has been set to a value of 1.4 such that the current magnification is equal to 1.429 and the corresponding depth in the object is 14.9 cm.

The "focusing" (that is to say the correct superposition of the sub-images) has not yet been carried out in the vertical diametrical plane of the ball.

Figure 9C:
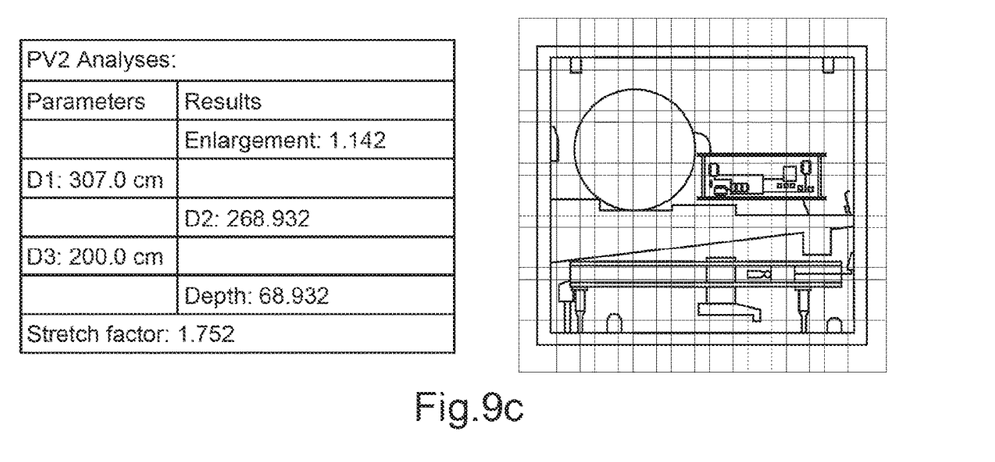

In FIG. 9c, the convergence plane of the ball is achieved for a stretch factor F=1.752, that is to say for a magnification by 1.142 and of a depth of nearly 69 cm.

The superposition of a shape in the convergence plane makes it possible measure the real size of the element of interest because its magnification is known. In the example represented here, the superposition of a circle on the disk representing the ball makes it possible to measure the diameter of the ball at 36.1 cm based on the number of pixels per centimeter which is known for the plane of magnification G=2.

All the elements of the object for which the focusing is correct on the image represented in FIG. 9c are in the vertical diametrical plane of the ball.

Figure 10:
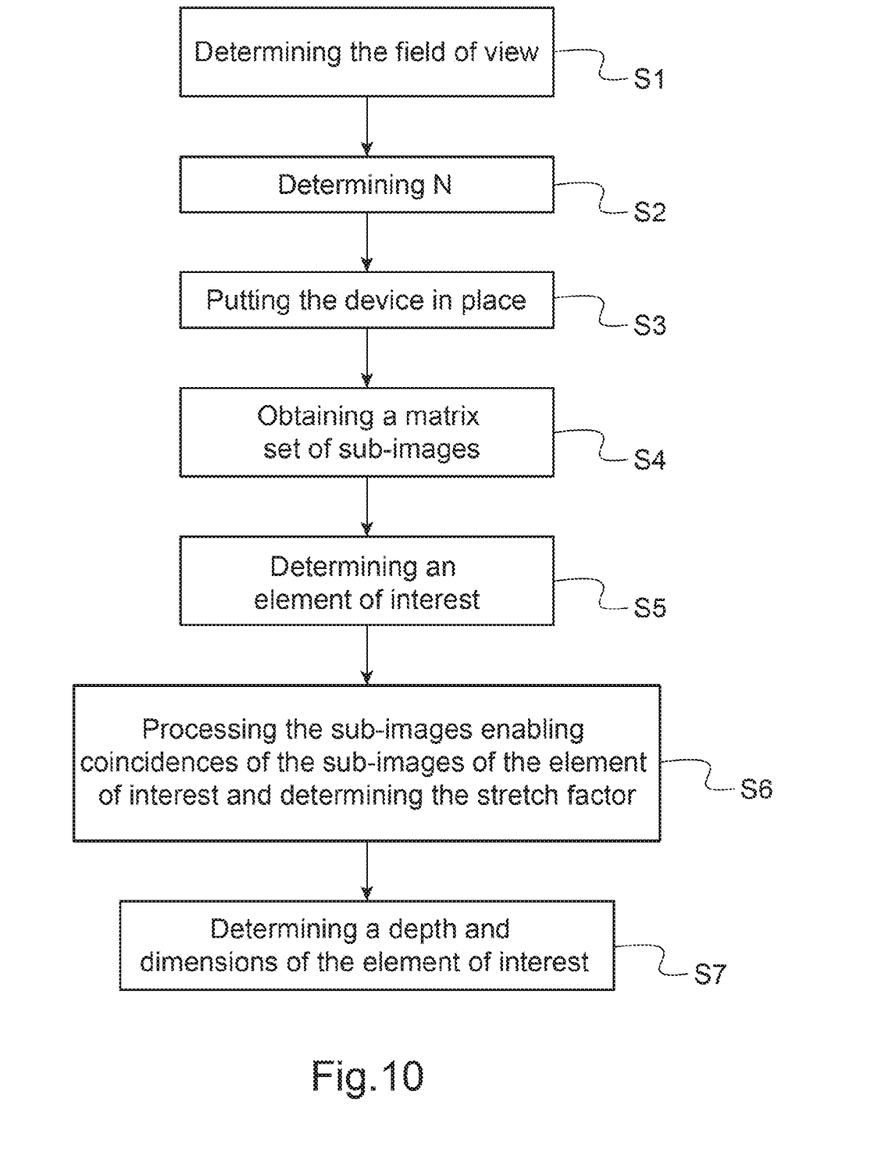
FIG. 10 illustrates in flow-chart form the steps of a method in accordance with a particular embodiment of the invention.

The invention also relates to a method of three-dimensional inspection of an object by X-rays, of which a particular example is illustrated in FIG. 10 which represents the succession of steps which can be implemented.

The method employs an apparatus in accordance with an embodiment of the invention.

The method comprises a step of determining the field of view necessary to X-ray an object to inspect (S1).

The integer N is next determined, by taking into consideration the available spacing away and dimensions of a region of interest containing the element of interest (S2). This step may be carried out according to the provisions described above with reference to FIGS. 2 and 3. It follows that:

if the region of interest is of greater dimension in the first direction than the fraction 1/N of the side of the imaging device corresponding to the first direction and is of greater dimension in the second direction than the fraction 1/N of the side of the imaging device corresponding to the second direction, N is the smallest integer, greater than 1, for which the spacing away is greater than 1/N times the distance between the X-ray generator and the imaging device, or if the region of interest is of smaller dimension in the first direction than the fraction 1/N of the side of the imaging device corresponding to the first direction or is of smaller dimension in the second direction than the fraction 1/N of the side of the imaging device corresponding to the second direction, N is the smallest integer for which the spacing away is greater than 2/N times the distance between the X-ray generator and the imaging device.

The apparatus is next put in place relative to the object to inspect (S3). In particular, the alignment of the X-ray generator is made relative to the imaging device, and the X-ray generator is positioned at the appropriate distance from the imaging device.

The number of movements in the first and the second direction to cover the field of view is determined. Next follows a step of obtaining a matrix set of sub-images (S4).

The sub-images are transferred onto a computer system such as a portable computer to be processed thereon. Various parameters are received in the processing software, such as the distance D1 between the X-ray generator and the imaging device, the distance D3 between the X-ray generator and the closest point of the object.

An element of interest is determined in said set of sub-images (S5).

The sub-images are processed, by homothetic magnification and partial superposition of the sub-images representing the whole or part of the element of interest, as described with reference to FIGS. 9a to 9c. This enables the determination of a stretch factor enabling the coincidence of the sub-images at the location of the point of interest. (S6).

The depth of the element of interest is next determined according to the stretch factor (S7). The dimensions of the element of interest may also be determined, as explained with reference to FIG. 9c.

By way of example embodiment, an apparatus according to the invention has been produced using an imaging device having a rectangular active surface of 40 cm by 28.5 cm. This apparatus is dimensioned so as to enable the coverage of a field of view of 120 cm by 114 cm. The apparatus produced has a mechanism for extending its vertical shaft making it possible to X-ray a field of view of 200 cm by 114 cm in two successive passes. The apparatus is foldable and transportable on a palette of 80 cm by 120 cm.

By way of a second example embodiment, an apparatus according to the invention has been produced using an imaging device having a rectangular active surface of 43 cm by 35 cm. This apparatus makes it possible to X-ray a field of view of 175 cm by 172 cm. This apparatus is foldable and for its transportation enables the members constituting the mountings employed to be aligned in a same plane.

Numerous configurations enabling the implementation of the invention may thus be envisioned.

The invention thus developed enables the three-dimensional radiographic inspection of objects, in particular objects which it is undesirable or not possible to move.

The invention is for example applicable to security applications in which the objects to X-ray cannot be moved to fixed installations and for the cases in which the object is of large dimension. For these applications, the minimization of the operation time and of the dose of X-rays deposited on the object are important criteria. Furthermore, the object sub-assemblies to analyze are of multi-centimeter size. For these applications, it is optimum (but not absolutely necessary) to use the invention with N=2.

The inspection by radiography of immobile vehicles had until now no ergonomic solution. On objects of such length, it is possible to perform radiography on the transverse axis but it is often impossible to perform it on the longitudinal axis while having information on depth in the vehicle. The invention makes it possible to mitigate this problem by enabling the access to the depth of the sub-assemblies on a single X-ray on the transverse axis.

The mobile radiography of containers of standard dimensions (so-called "ISO" containers) may be envisaged in automatized sequences and pyrotechnical objects of large dimensions may be inspected from the outside without taking the risk of using an endoscope as first-line action.

The invention enables non-destructive checks, in particular for imposing parts such as aircraft wings. For such checks, the implementation of the invention with N=3 is generally a suitable solution.

Lastly, the invention makes it possible to address technical issues which are not solved satisfactorily in the state of the art, such as the radiography of large animals (horses, cows, etc.) by an itinerary veterinarian.

The invention claimed is:

1. An apparatus for three-dimensional inspection of an object by X-rays, the apparatus comprising:
    an X-ray generator and a rectangular or square digital imaging device facing the X-ray generator,
    wherein the X-ray generator and the imaging device are spaced apart from each other by a distance corresponding to a magnification by 1, the X-ray generator is on an axis orthogonal to a plane of extension of the imaging device passing through a center of the imaging device, and
    wherein the X-ray generator is movable in a plane parallel to the plane of extension of the imaging device, and the imaging device is further movable within an X-ray generator plane of extension,
    the apparatus further comprising a means for controlling the position and the movement of the X-ray generator and of the imaging device and configured so as to move the X-ray generator by unitary movements in a first direction or a second direction respectively parallel to the sides of the imaging device and, at each unitary movement, to hold the relative position of the imaging device in relation to the X-ray generator,
    the control means being configured such that each unitary movement of the X-ray generator and of the imaging device, in the first or in the second direction, corresponds to an integer number fraction of a corresponding side of the imaging device, the integer number fraction is 1/N times the dimension of the side corresponding to the first direction and 1/N times the dimension of the side corresponding to the second direction, where N is a natural number greater than 1, so as to obtain, by successive shots after each unitary movement, a matrix set of sub-images overlapping in the plane of extension of the imaging device,
    wherein each sub-image has a center attributed with coordinates in a plane of magnification equal to N, the coordinates being determined according to the position of the center of the imaging device on taking the sub-image, and the apparatus further comprises an image processing means configured to perform a homothetic magnification of each sub-image, leaving unchanged the coordinates of the center of each sub-image, the image processing means further configured to determine a stretch factor enabling a coincidence of the sub-images representing all or some of a predefined element of interest of the image.

2. The apparatus according to claim 1, further comprising means for determining a depth and dimensions of the element of interest according to the determined stretch factor.

3. The apparatus according to claim 1, further comprising a first mounting and a second mounting, wherein, the first mounting bears the imaging device, and the second mounting bears the X-ray generator.

4. The apparatus according to claim 3, wherein the first mounting comprises motor-driven wheels, configured to move the imaging device in the first direction, and a positioning means for positioning the imaging device in the second direction comprising a telescopic member or an arm along which the imaging device can translate, and the second mounting comprises motor-driven wheels, configured to move the X-ray generator in the first direction, and a positioning means for positioning the X-ray generator in the second direction comprising a telescopic member or an arm along which the X-ray generator can translate.

5. The apparatus according to claim 3, wherein the first mounting comprises a first gantry and the second mounting comprises a second gantry, the first gantry comprising a first beam extending in the first direction and a member bearing the imaging device extending in the second direction and configured to position the imaging device in the second direction, the member bearing the imaging device being linked to the first beam so as to be able to be translated in the first direction, the member bearing the imaging device being a telescopic member or a second beam along which the imaging device is able to translate, the second gantry having a configuration identical to that of the first gantry and bearing the X-ray generator.

6. The apparatus according to claim 3, wherein the first mounting comprises a first gantry and the second mounting comprises a second gantry, the first gantry comprising a first telescopic member extending in the first direction and a second telescopic member bearing the imaging device extending in the second direction and configured to position the imaging device in the second direction, the second telescopic member being linked to the first telescopic member so as to be moved in the first direction by elongation or retraction of the first telescopic member, the second gantry having a configuration identical to that of the first gantry and bearing the X-ray generator.

7. The apparatus according to claim 5, wherein the first and the second mounting each comprise an anti-tipping foot comprising a third beam, rigidly linked substantially orthogonally to the first beam.

8. The apparatus according to claim 3, comprising a laser aligning device enabling the relative alignment of the first and second mountings.

9. The apparatus according to claim 1, comprising a structure rigidly linking the X-ray generator and the imaging device, the structure between the X-ray generator and the imaging device, the structure being carried by the mounting comprising a system for moving the structure in the first direction and in the second direction.

10. The apparatus according to claim 9, wherein the system for moving the structure comprises motor-driven wheels configured to move the structure in the first direction, and a mechanism comprising a telescopic member linked to the structure or an arm oriented in the second direction along which the structure is able to translate.

11. A method of three-dimensional inspection of an object by X-rays comprising the steps of:

providing an apparatus according to claim 1;

putting the apparatus in place in relation to the object, the X-ray generator and the imaging device being spaced from each other by a distance corresponding to a magnification by 1;

obtaining a matrix set of sub-images;

determining an element of interest of the object represented in the set of sub-images;

determining, by homothetic magnification and partial superposition of the sub-images representing all or part of the element of interest, a stretch factor enabling the coincidence of the sub-images at the location of a point of interest; and determining a depth and dimensions of the element of interest according to the determined stretch factor.

12. A method according to claim 11, further comprising, between providing the apparatus and putting the apparatus in place, a step of determining a field of view necessary to X-ray the object, a step of determining an available spacing away in relation to a front face of the object for the putting in place of the X-ray generator; and a step of determining N according to the available spacing away and the dimensions of a region of interest containing the element of interest.

13. The method according to claim 12, wherein N is determined such that:

if the region of interest has both a greater dimension in the first direction than the fraction 1/N of the side of the imaging device corresponding to the first direction and a greater dimension in the second direction than the fraction 1/N of the side of the imaging device corresponding to the second direction, then N is the smallest integer greater than 1, for which the spacing away is greater than 1/N times the distance between the X-ray generator and the imaging device, if the region of interest has both a smaller dimension in the first direction than the fraction 1/N of the side of the imaging device corresponding to the first direction or a smaller dimension in the second direction than the fraction 1/N of the side of the imaging device corresponding to the second direction, then N is the smallest integer for which the spacing away is greater than 2/N times the distance between the X-ray generator and the imaging device.

14. The method according to claim 12, wherein N=2 or N=3, and further comprising a step of determining a number of shots n necessary with the imaging device to cover a field of view, without superposition of images, in the first direction and a number of shots m necessary with the imaging device to cover the field of view, without superposition of images, in the second direction, and wherein the step of obtaining the matrix set of sub-images comprises obtaining N*n−3 to N*n+1 sub-images in the first direction and N*m−3 to N*m+1 sub-images in the second direction.

* * * * *